US012453808B2

(12) United States Patent
Madjarov et al.

(10) Patent No.: US 12,453,808 B2
(45) Date of Patent: Oct. 28, 2025

(54) CANNULA FOR APICAL CANNULATION

(71) Applicant: Jeko Metodiev Madjarov, Charlotte, NC (US)

(72) Inventors: Jeko Metodiev Madjarov, Wilmington, NC (US); Francis Robicsek, Charlotte, NC (US)

(73) Assignee: Jeko Metodiev Madjarov, Wilmington, NC (US)

( * ) Notice: Subject to any disclaimer, the term of this patent is extended or adjusted under 35 U.S.C. 154(b) by 408 days.

(21) Appl. No.: 17/775,103

(22) PCT Filed: Nov. 9, 2020

(86) PCT No.: PCT/US2020/059633
§ 371 (c)(1),
(2) Date: May 6, 2022

(87) PCT Pub. No.: WO2021/092539
PCT Pub. Date: May 14, 2021

(65) Prior Publication Data

US 2022/0387691 A1 Dec. 8, 2022

Related U.S. Application Data

(60) Provisional application No. 62/932,197, filed on Nov. 7, 2019.

(51) Int. Cl.
*A61M 1/36* (2006.01)
*A61M 25/00* (2006.01)
*A61M 25/10* (2013.01)

(52) U.S. Cl.
CPC ........ *A61M 1/3659* (2014.02); *A61M 25/003* (2013.01); *A61M 2025/0031* (2013.01); *A61M 2025/1052* (2013.01)

(58) Field of Classification Search
CPC .............. A61M 1/3659; A61M 25/003; A61M 2025/0031; A61M 2025/1052; A61M 60/178; A61M 60/00
See application file for complete search history.

(56) References Cited

U.S. PATENT DOCUMENTS 6,582,388 B1 * 6/2003 Coleman ............ A61M 25/003 604/8
2001/0003795 A1 6/2001 Suresh et al.
(Continued)

FOREIGN PATENT DOCUMENTS

DE 102018104168 B3 * 3/2019 .......... A61M 25/003
EP 2739347 B2 7/2016
(Continued)

OTHER PUBLICATIONS

International Search Report and Written Opinion for PCT/US2020/059633 (ISA/US) mailed Feb. 3, 2021.
(Continued)

*Primary Examiner* — Jessica Arble
(74) *Attorney, Agent, or Firm* — Alston & Bird LLP

(57) ABSTRACT

Cannulas for apical cannulation and methods of making and using the same are provided. The cannula includes a first elongated body defining a primary lumen, a second elongated body defining a first secondary lumen, a third elongated body defining a second secondary lumen, and a fourth elongated body defining a third secondary lumen. The primary lumen is configured to allow blood to flow therethrough. The first secondary lumen is configured to inflate an inflatable body, which is configured to engage an aortal wall proximate the aortic valve of the patient's heart to define a treatment space. The second secondary lumen is configured to selectively remove blood from the treatment space or introduce a cardioplegic solution into the treatment space.
(Continued)

The third secondary lumen is configured to administer active decompression of the left ventricle of the patient's heart via suction.

20 Claims, 5 Drawing Sheets

(56) References Cited

U.S. PATENT DOCUMENTS

| | | | | |
|---|---|---|---|---|
| 2004/0059277 | A1* | 3/2004 | Maguire | A61M 25/10 604/104 |
| 2005/0085761 | A1 | 4/2005 | Wang et al. | |
| 2006/0270892 | A1 | 11/2006 | Bolling et al. | |
| 2012/0296152 | A1 | 11/2012 | Reichenbach et al. | |
| 2016/0101230 | A1 | 4/2016 | Ochsner et al. | |
| 2016/0263356 | A1* | 9/2016 | Selim | A61M 1/3667 |
| 2016/0296683 | A1* | 10/2016 | Jin | A61M 60/857 |
| 2018/0228960 | A1 | 8/2018 | Marous, III et al. | |
| 2020/0405943 | A1* | 12/2020 | Menon | A61M 1/32 |
| 2021/0260354 | A1* | 8/2021 | Tamari | A61M 60/279 |
| 2024/0108852 | A1* | 4/2024 | Milano | A61M 25/0045 |

FOREIGN PATENT DOCUMENTS

| | | |
|---|---|---|
| WO | WO 99/58174 A2 | 11/1999 |
| WO | WO 99/58174 A3 | 1/2000 |

OTHER PUBLICATIONS

Extended European Search Report for European Patent Application No. 20884946.3 dated Jan. 2, 2024 (9 pages).

Extended European Search Report for EP Patent Application No. 24200035.4 dated Jan. 28, 2025 (13 pages).

* cited by examiner

CANNULA FOR APICAL CANNULATION

CROSS-REFERENCE TO RELATED APPLICATION

The present application claims the benefit of priority of U.S. Provisional Patent Application No. 62/932,197 filed on Nov. 7, 2019, the entire contents of which are hereby incorporated by reference in their entirety for all purposes.

FIELD

The presently-disclosed invention relates generally to cannulas for apical cannulation and methods of making and using the same, and more particularly to cannulas for apical cannulation that perform multiple functions for apical cannulation using a single cannula without additional cannulas or other instruments and methods of making and using the same.

BACKGROUND

The standard approach for cannulation for arterial return flow in connection with cardio-pulmonary bypass (CPB) is through the aorta or one of its tributaries. An alternative to arterial cannulation is to introduce the arterial-return cannula through the apex of the left ventricle and advance it into the aortic arch. This approach is used primarily when arterial cannulation does not appear to be feasible due to poor quality of the vessel, or if cannulation of the aorta seems inadvisable due to aortic dissection, among other reasons.

Besides avoiding handling a calcified or dissected aorta or its branches, apical cannulation is advantageous because it may be rapidly performed, virtually assures that in the case of aortic dissection the cannula is in the natural lumen, and allows for easy reinsertion, if necessary.

One problem with apical cannulation is that it typically requires the use of multiple cannulas and/or instruments to carry out the necessary functions, including occluding the aorta, introducing cardioplegic solution, and applying suction to the left ventricle.

Accordingly, there still exists a need for a cannula for apical cannulation that performs the necessary functions required for apical cannulation without additional cannulas or other instruments.

BRIEF SUMMARY

One or more embodiments of the invention may address one or more of the aforementioned problems. Certain embodiments according to the invention provide cannulas for apical cannulation that perform the functions generally required for apical cannulation, including occluding the aorta, introducing cardioplegic solution, and applying suction to the left ventricle, without additional cannulas or other instruments. In particular, according to a first aspect of the invention, a cannula configured to be positioned in a patient's heart for apical cannulation is provided. The cannula includes a first elongated body defining a primary lumen, a second elongated body defining a first secondary lumen, a third elongated body defining a second secondary lumen, and a fourth elongated body defining a third secondary lumen. The primary lumen is configured to allow blood to flow therethrough. The first secondary lumen is in fluid communication with a source of inflation media and with an inflatable body attached to the cannula proximate a distal end of the first elongated body and is configured to inflate the inflatable body, which is configured to engage an aortal wall proximate the aortic valve of the patient's heart to define a treatment space. The second secondary lumen is configured to selectively remove blood from the treatment space or introduce a cardioplegic solution into the treatment space. The third secondary lumen is configured to administer active decompression of the left ventricle of the patient's heart via suction.

According to certain embodiments, the first elongated body may be integral with at least one of the second elongated body, the third elongated body, or fourth elongated body. In some embodiments, at least one of the second elongated body, the third elongated body, or the fourth elongated body may be disposed within the first elongated body.

According to certain embodiments, the first elongated body may define at least one opening in fluid communication with the first secondary lumen to allow the inflation media to pass therethrough. In some embodiments, the first elongated body may define at least one opening in fluid communication with the second secondary lumen to allow blood or the cardioplegic solution to pass therethrough. In further embodiments, the first elongated body may define at least one opening in fluid communication with the third secondary lumen to allow blood to pass therethrough.

According to certain embodiments, the cannula may be configured to serve as an arterial limb of a cardio-pulmonary bypass circuit. In other embodiments, the cannula may be configured to serve as a left ventricular assist device. In further embodiments, the cannula may be configured to serve as a venal-arterial ECMO circuit. In some embodiments, each of the first secondary lumen, the second secondary lumen, and the third secondary lumen may be selectively operational.

According to certain embodiments, the cannula may comprise polyethylene terephthalate. In some embodiments, the first elongated body may comprise a plurality of radiopaque markers disposed on an exterior surface of a peripheral wall of the first elongated body.

According to certain embodiments, the second elongated body may have a length that is shorter than a length of the first elongated body. In some embodiments, the third elongated body may have a length that is shorter than a length of the second elongated body and the first elongated body. In further embodiments, the fourth elongated body may have a length that is shorter than a length of the third elongated body, the second elongated body, and the first elongated body.

In accordance with a second aspect of the invention, a method of making a cannula configured to be positioned in a patient's heart for apical cannulation is provided. The method includes forming a first elongated body defining a primary lumen configured to allow blood to flow therethrough, providing a second elongated body supported by the first elongated body, providing a third elongated body supported by the first elongated body, and providing a fourth elongated body supported by the first elongated body. The second elongated body defines a first secondary lumen configured to inflate an inflatable body. The third elongated body defines a second secondary lumen configured to selectively remove blood from the treatment space or introduce a cardioplegic solution into the treatment space. The fourth elongated body defines a third secondary lumen configured to administer active decompression of the left ventricle of the patient's heart via suction.

According to certain embodiments, at least one of the second elongated body, the third elongated body, and the fourth elongated body may be disposed on an interior surface of a peripheral wall of the first elongated body. In some embodiments, at least one of the second elongated body, the third elongated body, and the fourth elongated body may be disposed on an exterior surface of a peripheral wall of the first elongated body.

In accordance with a third aspect of the invention, a method of apical cannulation is provided. The method includes positioning a cannula in the aortic arch via the apex of the left ventricle. The cannula comprises a first elongated body defining a primary lumen, wherein the primary lumen is configured to allow blood to flow therethrough; a second elongated body defining a first secondary lumen, wherein the first secondary lumen is in fluid communication with a source of inflation media and with an inflatable body attached to the cannula proximate a distal end of the first elongated body; a third elongated body defining a second secondary lumen; and a fourth elongated body defining a third secondary lumen. The method further comprises inflating the inflatable body via the second elongated body to engage an aortal wall proximate the aortic valve of the patient's heart to define a treatment space, selectively removing blood from the treatment space or introducing a cardioplegic solution into the treatment space via the third elongated body, and decompressing the left ventricle of the patient's heart via suction through the fourth elongated body. According to certain embodiments, the method may further comprise selectively operating the cannula as at least one of an arterial limb of a cardio-pulmonary bypass circuit, a left ventricular assist device, or a venal-arterial ECMO circuit.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

The invention includes, according to certain embodiments, cannulas for apical cannulation that perform multiple functions generally required for apical cannulation, including occluding the aorta, introducing cardioplegic solution, and applying suction to the left ventricle using a single cannula, without additional cannulas or other instruments. In particular, according to a first aspect of the invention, a cannula configured to be positioned in a patient's heart for apical cannulation is provided. The cannula includes a first elongated body defining a primary lumen, a second elongated body defining a first secondary lumen, a third elongated body defining a second secondary lumen, and a fourth elongated body defining a third secondary lumen. The primary lumen is configured to allow blood to flow therethrough. The first secondary lumen is in fluid communication with a source of inflation media and with an inflatable body attached to the cannula proximate a distal end of the first elongated body and is configured to inflate the inflatable body, which is configured to engage an aortal wall proximate the aortic valve of the patient's heart to define a treatment space. The second secondary lumen is configured to selectively remove blood from the treatment space or introduce a cardioplegic solution into the treatment space. The third secondary lumen is configured to administer active decompression of the left ventricle of the patient's heart via suction.

Figure 1:
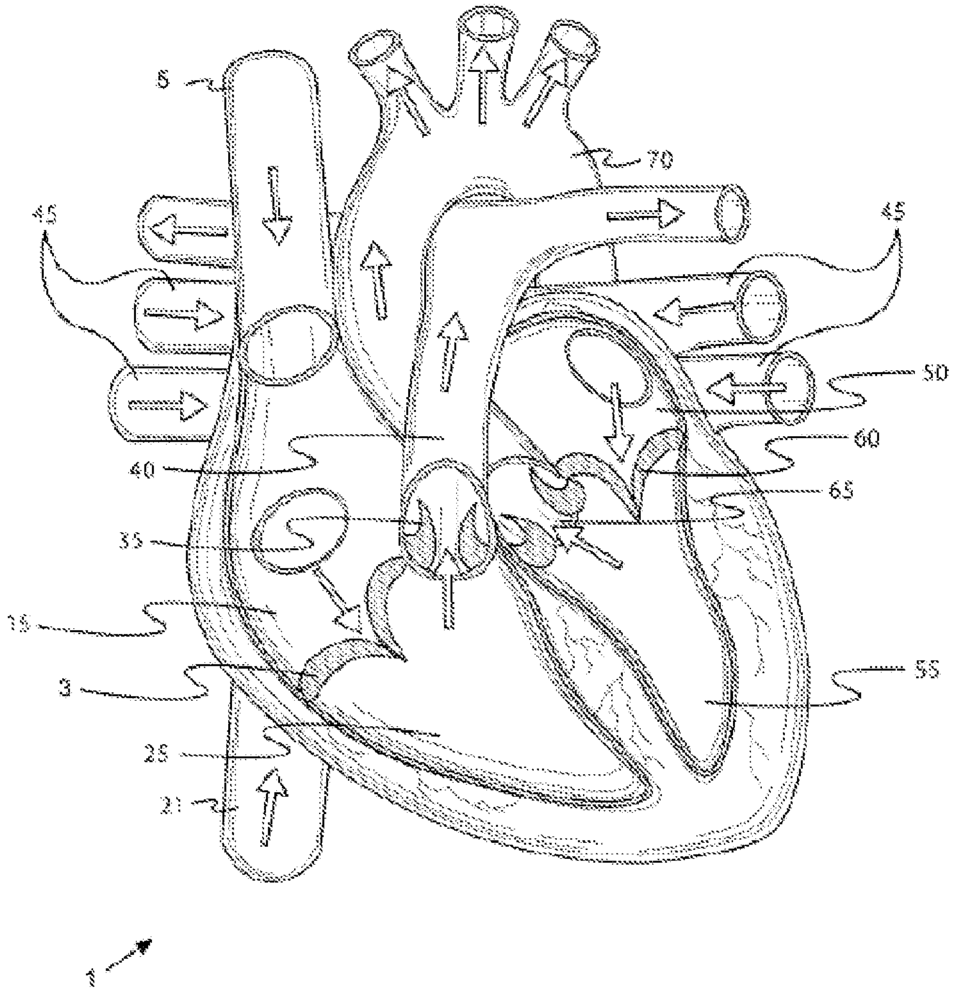
FIG. 1 shows a schematic representation of a heart illustrating its various chambers and valves.

With reference to FIG. 1, the path of circulation of blood through the heart 1 will be described. In the human body, deoxygenated blood enters the right atrium 15 of the heart 1 via the superior vena cava 5 (from the upper half of the body) and the inferior vena cava 21 (from the lower half of the body). Once the right atrium 15 is full of blood, the pressure difference between the right atrium and the right ventricle 25 causes the tricuspid valve 3 to open, allowing blood to flow into the right ventricle 25. As the right ventricle 25 contracts, blood is pushed through the pulmonary valve 35 and into the lungs via the pulmonary artery 40, where the blood is re-oxygenated. Oxygenated blood from the lungs can then re-enter the heart 1 via the pulmonary veins 45 into the left atrium 50. The pressure differential between the left atrium 50 and the left ventricle 55 when the left atrium fills with blood then causes the mitral valve 60 to open, and blood is allowed to flow from the left atrium to the left ventricle. Finally, contraction of the left ventricle 55 forces the aortic valve 65 to open and pushes blood into the aorta 70, from which oxygenated blood is circulated through the vasculature.

Figure 2:
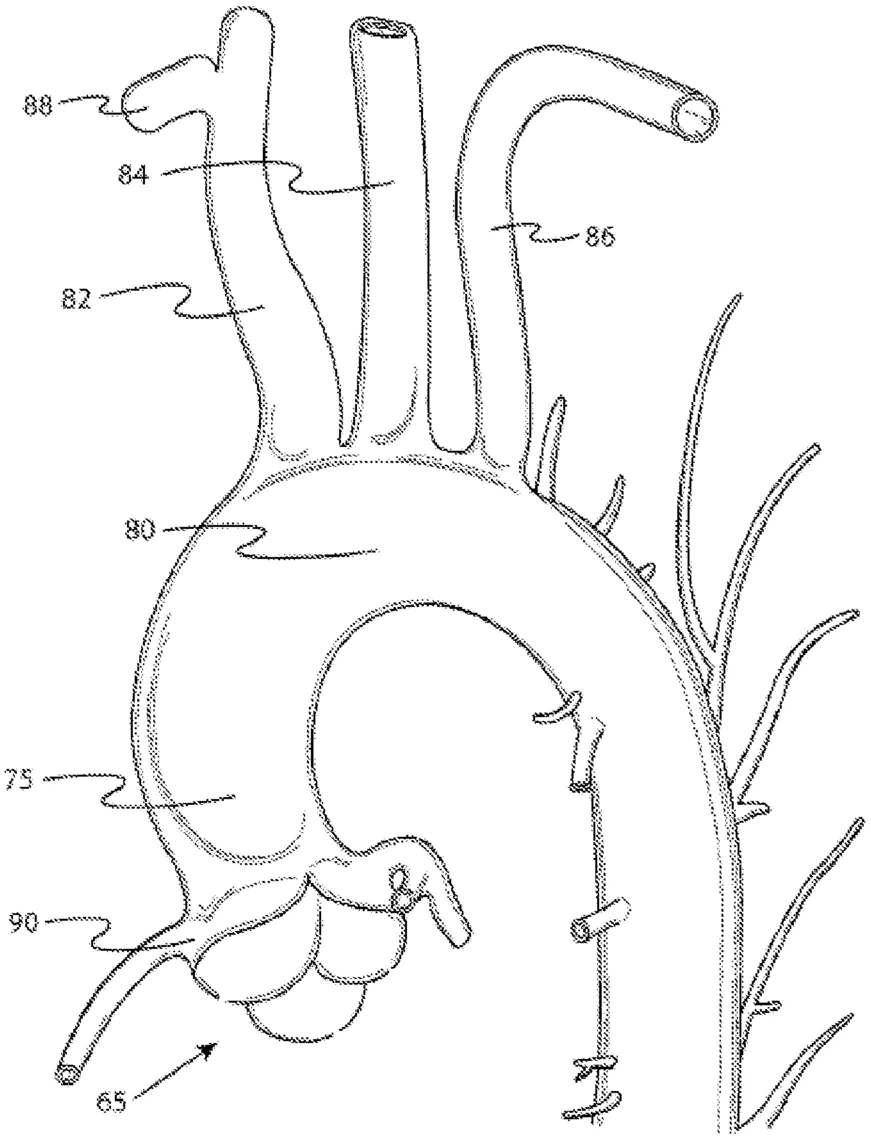
FIG. 2 shows a schematic representation of an aortic valve and aortic arch.
Figure 3:
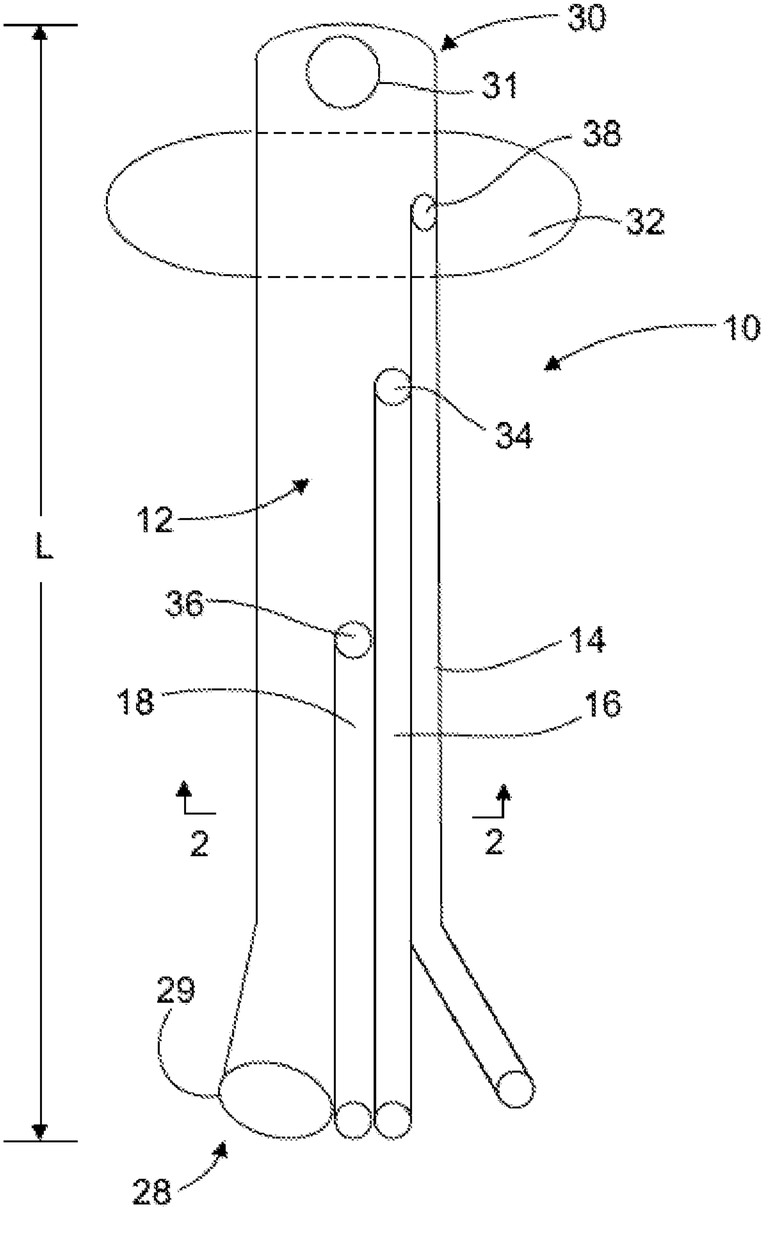
FIG. 3 is a side view of a cannula in accordance with certain embodiments of the invention.

With reference to FIG. 2, the ascending aorta 75 is the portion of the aorta 70 that starts at the upper part of the base of the left ventricle and extends to the aortic arch 80, where the right common carotid artery 82, the left common carotid artery 84, and the left subclavian artery 86 (and in rare cases, the right subclavian artery 88) branch out to provide oxygenated blood to the upper thorax and the brain. The aortic root 90 is the part of the ascending aorta 75 that begins at the aortic annulus and extends to the sinotubular junction, where the aorta begins to have a tubular structure.

FIGS. 3, 4A, 4B, and 5 illustrate an example surgical cannula 10 according to embodiments of the invention, which has a primary lumen 12 and incorporates, in this example configuration, first, second, and third secondary lumens labeled 14, 16, and 18, respectively. The primary lumen 12 is formed by a closed peripheral wall 20 of the first elongated body defining an internal bore 22, which may be circular or some other convenient cross-sectional shape. The peripheral wall 20 has opposed interior and exterior surfaces 24, 26 respectively (shown in FIGS. 4A and 4B). The peripheral wall 20 may be homogenous or may be made of multiple layers of the same or different materials.

The cannula 10 has an overall length "L" measured from base 28, which spans the length from an inlet 29, to a tip 30 and includes an outlet 31 defined in the first elongated body. The length L may be sufficient to extend from the apex of the heart (that is, the tip of the left ventricle, opposite the base of the heart) to the descending aorta, thus decreasing the danger of embolization to the brain. In some embodiments, the first secondary lumen 14 may be shorter than the primary lumen 12. In certain embodiments, the second secondary lumen 16 may be shorter than the primary lumen 12 and the first secondary lumen 14. In further embodiments, the third secondary lumen 18 may be shorter than the primary lumen 12, the first secondary lumen 14, and the second secondary lumen 16. Notably, each of the primary lumen 12, the first secondary lumen 14, the second secondary lumen 16, and the third secondary lumen 18 is fluidly isolated from the other lumens, such that the lumens are not in fluid communication with each other and the fluids flowing through each do not mix.

Figure 4A:
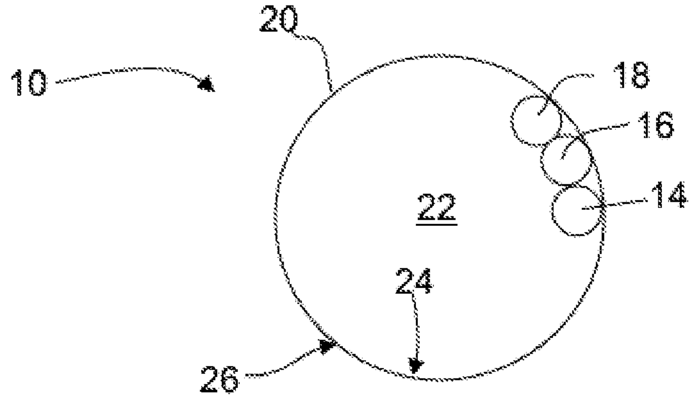
FIGS. 4A and 4B are schematic section views taken along lines 2-2 of FIG. 3 in accordance with certain embodiments of the invention.

The size (e.g. inside diameter) of the first elongated body defining the primary lumen 12, alternatively referred to as its caliber, is selected to permit arterial-return blood flow "F" and also optionally to allow the three other elongated bodies defining the three secondary lumens 14, 16, 18 to be included in the interior of the primary lumen 12, as shown in FIG. 4A. For example, the diameter of the primary lumen 12 may be about 8 mm to 28 mm, such as, for example, 12 mm. In this way, the primary lumen 12 may be an arterial limb of a CPB circuit and, as such, may be configured to pump blood to a heart-lung machine that cleans and oxygenates the blood before returning the blood to the body.

An inflatable body 32 (e.g., a balloon) surrounds the first elongated body defining the primary lumen 12 and is attached to the first elongated body about 20 cm to 30 cm from the base 28, proximate the distal end of the primary lumen 12. The inflatable body 32 is in fluid communication with the first secondary lumen 14, which may be of small caliber (e.g., 2 mm). The inflatable body 32 may have an inflated volume of about 25 cc.

Figure 5:
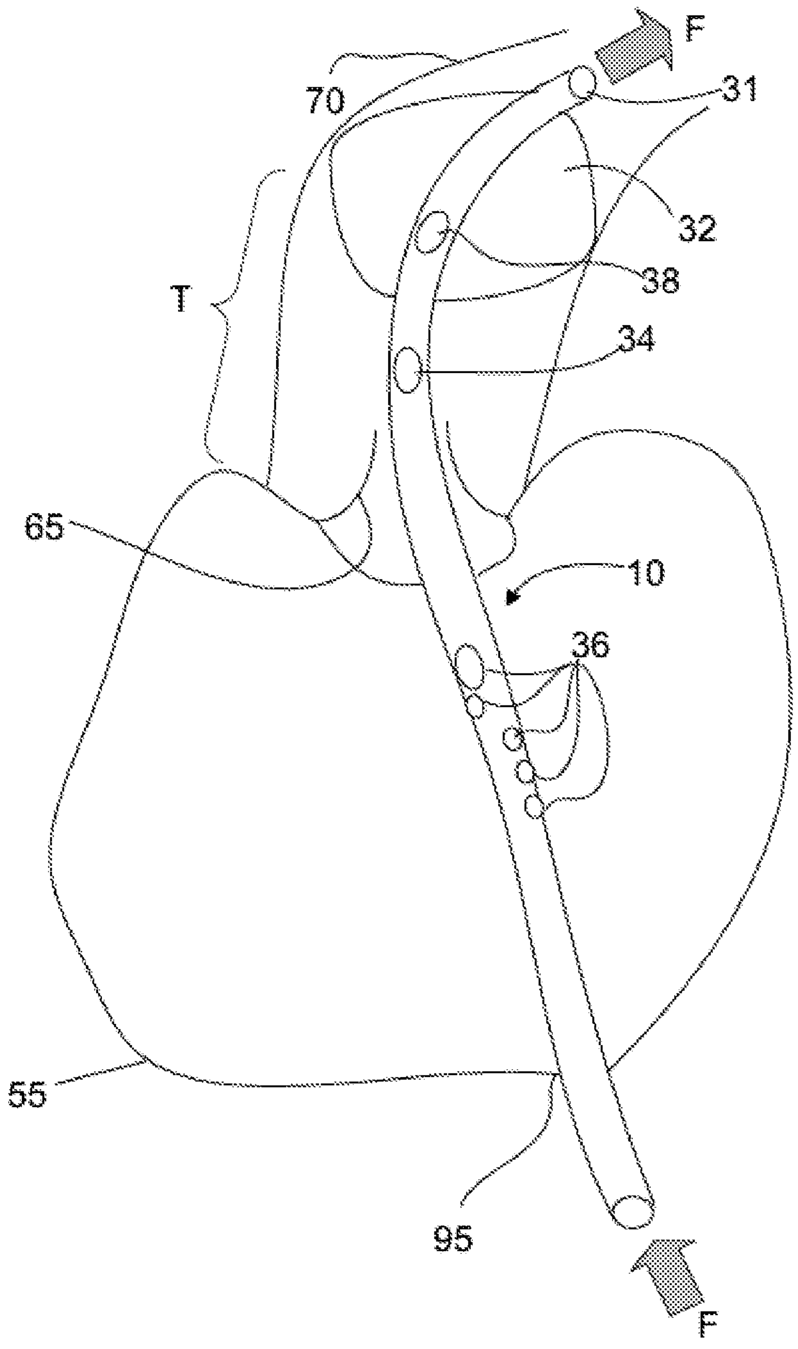
FIG. 5 illustrates a cannula inserted into a heart using an apical approach in accordance with certain embodiments of the invention.

In use, the inflatable body 32 may be inflated using an inflation medium (e.g., a pressurized fluid such as air, other gas, or liquid) supplied through the first secondary lumen 14 and a distal opening 38 formed in the second elongated body. In some cases, the first elongated body defines at least one opening in fluid communication with the first secondary lumen to allow the inflation media to pass therethrough. For example, the distal opening 38 may align with an opening defined by the peripheral wall 20 of the first elongated body (e.g., in an embodiment in which the second elongated body defining the first secondary lumen 14 is disposed within the first elongated body, or within the peripheral wall 20) to allow the inflation medium to pass through to the inflatable body 32. In this way, the inflation medium is kept separate from the blood and no mixing is allowed, thereby maintaining the lumens separate and fluidly isolated from each other. As seen in FIG. 5, inflation of the inflatable body 32 may occlude the entire lumen of the aorta 70 to define a treatment space T between the aortic valve 65 and the base of the inflated inflatable body 32, allowing retention of intracoronary cardioplegic solution while also making aortic cross-clamping unnecessary in cases requiring the opening of the ascending aorta to repair ascending aortic pathology.

The third elongated body defining the second secondary lumen 16 may have a distal opening 34 located near the inflatable body 32. It may be of small caliber (e.g., 2 mm to 6 mm). In use, as seen in FIG. 5, the distal end 34 may lie in the area between the aortic valve 65 and inflatable body 32. The second secondary lumen 16 may be used to administer cardioplegic solution in the treatment space T or to remove blood with active suction from the treatment space (via the distal opening 34), for example, in preparation for administering the cardioplegic solution. In some embodiments, such as when the third elongated body is disposed within the first elongated body, the first elongated body may define at least one opening in fluid communication with the second secondary lumen to allow the blood or the cardioplegic solution to pass therethrough.

The fourth elongated body defining the third secondary lumen 18 has at least one distal opening 36 terminating between the inflatable body 32 and the base 28. It may be of small caliber (e.g., 2 mm to 16 mm). In use, as seen in FIG. 5, the distal opening(s) 36 may lie in the left ventricle 55. The third secondary lumen 18 may be used for active decompression of the left ventricle 55 via suction through the distal opening(s) 36 to avoid distension (e.g., from pooled blood) in the left ventricle 55. In some embodiments, and as illustrated in FIG. 5, the third secondary lumen 18 may have a plurality of distal openings 36, with some of the distal openings being positioned on one side of the third secondary lumen 18 and other distal openings being positioned on the opposite side of the third secondary lumen 18. In this way, the third secondary lumen 18 may be able to suction more blood from the left ventricle 55 with more openings. Any blood suctioned from the left ventricle 55 via the third secondary lumen 18 may be transferred to the heart-lung machine and cleaned/oxygenated with the blood removed through the primary lumen 12. In some embodiments in which the fourth elongated body is disposed within the first elongated body, the first elongated body may define at least one opening in fluid communication with the third secondary lumen to allow blood to pass therethrough.

The cannula 10 may be formed from a biocompatible material, that is, a material which is not harmful to living tissue. Known biocompatible materials include certain polymers, such as polyethylene terephthalate (PETE). The construction may be, for example, extruded or molded. In some embodiments, the first elongated body defining the primary lumen 12 may comprise a plurality of radiopaque markers (not shown) disposed on an exterior surface of the peripheral wall 20. Moreover, the ends of each of the first elongated body defining the primary lumen 12 and the second, third, and fourth elongated bodies defining the secondary lumens 14, 16, 18, as well as any side holes formed in the elongated bodies to allow fluid carried by the secondary lumens disposed within the first elongated body to pass through the peripheral wall, may be radiopaque to assist the operator in visualizing the cannula via fluoroscopy for proper insertion, manipulation, and operation of the cannula during the procedure being performed on the patient.

Figure 4B:
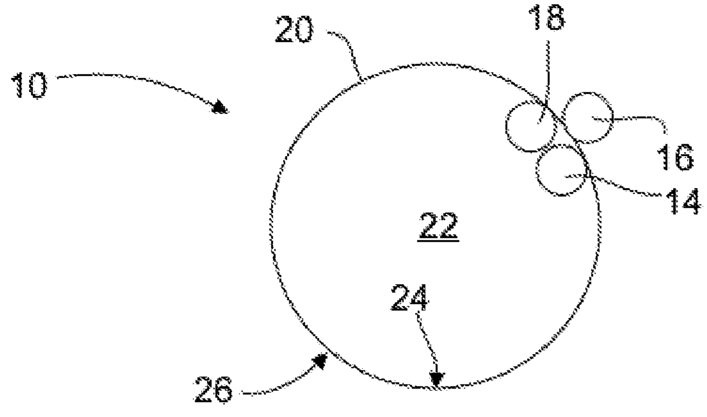

As described above, one or more of the elongated bodies defining the secondary lumens 14, 16, 18 may be attached to the outer surface of the elongated body defining the primary lumen 12, as shown in FIG. 4B, or may be disposed in its interior, as shown in FIG. 4A. For example, the third elongated body defining the second secondary lumen 16 may be outside the first elongated body defining the primary lumen 12, while the second elongated body defining the first secondary lumen 14 and the fourth elongated body defining the third secondary lumen 18 may be disposed inside the first elongated body defining the primary lumen 12. The entire cannula 10 may be formed integrally (e.g. by extrusion or molding the first, second, third, and fourth elongated bodies together) or the elongated bodies may be formed separately and then joined together. In some embodiments, the first elongated body defining the primary lumen 12 may thus be integral with at least one of the second, third, or fourth elongated bodies defining the secondary lumens 14, 16, 18.

In alternative embodiments, only one or two of the secondary lumens 14, 16, 18 may be incorporated into the cannula 10.

In a second aspect of the invention, a method of making a cannula configured to be positioned in a patient's heart for apical cannulation is provided. The method comprises forming a first elongated body defining a primary lumen configured to allow blood to flow therethrough, providing a second elongated body supported by the first elongated body, providing a third elongated body supported by the first elongated body, and providing a fourth elongated body supported by the first elongated body. As discussed previously herein, the second elongated body defines a first secondary lumen configured to inflate an inflatable body, the third elongated body defines a second secondary lumen configured to selectively remove blood from the treatment space or introduce a cardioplegic solution into the treatment space, and the fourth elongated body defines a third secondary lumen configured to administer active decompression of the left ventricle of the patient's heart via suction, as discussed above with reference to the figures.

According to certain embodiments, and as shown in FIG. 4A discussed above, at least one of the elongated bodies defining the first secondary lumen 14, the second secondary lumen 16, and the third secondary lumen 18 may be disposed on interior surface 24 of peripheral wall 20 of the first elongated body defining the primary lumen 12. In some embodiments, and as shown in FIG. 4B discussed above, at least one of the elongated bodies defining the first secondary lumen 14, the second secondary lumen 16, and the third secondary lumen 18 may be disposed on exterior surface 26 of peripheral wall 20 of the first elongated body defining the primary lumen 12.

In a third aspect of the invention, a method of apical cannulation is provided. The method includes positioning a cannula in the aortic arch via the apex of the left ventricle of a patient's heart and securing the cannula to the heart tissue at the entry point, for example, by conventional methods (e.g., a purse-string suture). As previously discussed herein, the cannula comprises a first elongated body defining a primary lumen, wherein the primary lumen is configured to allow blood to flow therethrough; a second elongated body defining a first secondary lumen, wherein the first secondary lumen is in fluid communication with a source of inflation media and with an inflatable body attached to the cannula proximate a distal end of the first elongated body; a third elongated body defining a second secondary lumen; and a fourth elongated body defining a third secondary lumen, as discussed above with reference to the figures. The method of apical cannulation further includes inflating the inflatable body via the second elongated body to engage an aortal wall proximate the aortic valve of the patient's heart to define a treatment space, selectively removing blood from the treatment space or introducing a cardioplegic solution into the treatment space via the third elongated body, and decompressing the left ventricle of the patient's heart via suction through the fourth elongated body.

According to certain embodiments, the method may further comprise selectively operating the cannula as at least one of an arterial limb of a CPB circuit, a left ventricular assist device (LVAD), or a VA-ECMO circuit. To transition among operating as an arterial limb of a CPB circuit, an LVAD, and a VA-ECMO circuit, each of the secondary lumens 14, 16, 18 may be selectively operational. For example, in some embodiments, the cannula 10 may temporarily operate as an LVAD for approximately 7-14 days, when the heart is too weak to function properly after surgery and to allow adequate recovery of the failing left ventricle. In such embodiments, the third secondary lumen 18 may continue to be operational, such that ventricular decompression continues to be provided to assist the heart's functioning, and the second secondary lumen 16 may, in some cases, also continue to be operational to deliver drugs, as needed. The first secondary lumen 14, however, may not be needed in such cases, as the inflatable body 32 would be deflated to allow oxygenated blood to pass naturally through the aortic valve and through the aorta to the patient's body.

Modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A left ventricular assist device for a patient's heart comprising:

a cannula, wherein the cannula is configured to function as part of the left ventricular assist device with a primary lumen having a diameter between a range of 8 mm to 28 mm and a secondary lumen having a diameter between a range of 2 mm and 16 mm, wherein the primary lumen comprises an inlet port at a distal end and an outlet port at a proximal end and routes blood flow through an internal bore between the inlet and outlet ports, and wherein the secondary lumen is disposed within the internal bore of the primary lumen and comprises a decompression opening defined along a length of the secondary lumen, the decompression opening in fluid communication with an opening defined by the primary lumen.

2. The left ventricular assist device of claim 1, wherein secondary lumen provides suction through the decompression opening during use.

3. The left ventricular assist device of claim 1, wherein the cannula has a configuration dimensioned to be introduced through an apex of the patient's heart into the aortic arch of the patient's heart.

4. The left ventricular assist device of claim 3, wherein a length of the cannula is dimensioned to extend from the apex of the patient's heart to the descending aorta.

5. The left ventricular assist device of claim 1, wherein the primary lumen is integral with the secondary lumen.

6. The left ventricular assist device of claim 1, wherein the secondary lumen is attached to an interior surface of a peripheral wall defining the internal bore of the primary lumen.

7. The left ventricular assist device of claim 1, wherein the cannula is configured to serve as the left ventricular assist device for between 7 and 14 days after surgery.

8. The left ventricular assist device of claim 1, wherein the primary lumen comprises a plurality of radiopaque markers disposed on an exterior surface of a peripheral wall of the primary lumen.

9. The left ventricular assist device of claim 1, wherein the diameter of the secondary lumen is at least half the size of the diameter of the primary lumen.

10. The left ventricular assist device of claim 9, wherein the diameter of the primary lumen is 12 mm.

11. A method of making a cannula configured to function as a left ventricular assist device, the method comprising:

forming a primary lumen with a primary lumen diameter, wherein the primary lumen defines an internal bore to allow blood to flow therethrough and an opening along its length;

providing a secondary lumen with a secondary lumen diameter, wherein the secondary lumen is positioned within the internal bore of the primary lumen and comprises a decompression opening defined along a length of the secondary lumen, the decompression opening in fluid communication with the opening defined by the primary lumen such that the secondary lumen is configured to administer active decompression of a left ventricle of a patient's heart, wherein the primary lumen diameter and the secondary lumen diameter are configured to provide respective blood flow rates that are sufficient to support the cannula serving as the left ventricular assist device.

12. The method of claim 11, wherein, during use as the left ventricular assist device, the active decompression of the left ventricle of the patient's heart is administered via suction.

13. The method of claim 11, wherein, during use as the left ventricular assist device, the cannula is introduced through an apex of the patient's heart into the aortic arch of the patient's heart.

14. The method of claim 13, wherein forming the primary lumen comprises forming an elongated body having a length dimensioned to extend from the apex of the patient's heart to the descending aorta.

15. The method of claim 11, wherein forming the primary lumen and providing the secondary lumen comprises integrally forming the primary lumen with the secondary lumen.

16. The method of claim 11, wherein providing the secondary lumen comprises attaching the secondary lumen to an interior surface of a peripheral wall defining the internal bore of the primary lumen.

17. The method of claim 11, wherein the cannula is configured to serve as the left ventricular assist device for between 7 and 14 days after surgery.

18. The method of claim 11, wherein the primary lumen comprises a plurality of radiopaque markers disposed on an exterior surface of a peripheral wall of the primary lumen.

19. The method of claim 11, wherein the primary lumen diameter is between 8 mm to 28 mm and the secondary lumen diameter is between a range of 2 mm and 16 mm.

20. A left ventricular assist device for a patient's heart comprising:

a cannula with a primary lumen and a secondary lumen, the secondary lumen having a diameter between a range of 2 mm and 16 mm, wherein the primary lumen comprises an inlet port at a distal end and an outlet port at a proximal end and routes blood flow through an internal bore between the inlet and outlet ports, and wherein the secondary lumen is disposed within the internal bore of the primary lumen and comprises a decompression opening defined along a length of the secondary lumen, the decompression opening in fluid communication with an opening defined by the primary lumen.

* * * * *